(12) United States Patent
Ritzberger et al.

(10) Patent No.: US 7,371,702 B2
(45) Date of Patent: May 13, 2008

(54) TRANSLUCENT AND RADIO-OPAQUE GLASS CERAMICS

(75) Inventors: Christian Ritzberger, Nenzing (AT); Elke Apel, Sevelen (CH); Wolfram Holand, Schaan (LI); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 75 days.

(21) Appl. No.: 11/357,780

(22) Filed: Feb. 17, 2006

(65) Prior Publication Data

US 2006/0205582 A1    Sep. 14, 2006

Related U.S. Application Data

(62) Division of application No. 10/932,245, filed on Sep. 1, 2004, now Pat. No. 7,183,232.

(30) Foreign Application Priority Data

Sep. 1, 2003 (DE) ................................ 103 40 597

(51) Int. Cl.
*C03C 10/06* (2006.01)
*A61C 13/00* (2006.01)

(52) U.S. Cl. ............................ 501/10; 65/33.3; 106/35; 433/228.1

(58) Field of Classification Search ................... 501/10; 106/35; 433/212.1; 65/33.3
See application file for complete search history.

(56) References Cited

U.S. PATENT DOCUMENTS

| | | | | |
|---|---|---|---|---|
| 4,536,480 A | * | 8/1985 | Flannery et al. | 501/32 |
| 4,536,481 A | * | 8/1985 | Flannery et al. | 501/32 |
| 5,304,577 A | * | 4/1994 | Nagata et al. | 524/417 |
| 5,952,253 A | * | 9/1999 | Dejneka et al. | 501/3 |
| 6,200,137 B1 | * | 3/2001 | Holand et al. | 433/212.1 |
| 6,280,863 B1 | * | 8/2001 | Frank et al. | 428/701 |

FOREIGN PATENT DOCUMENTS

JP          06039031          *  2/1994

* cited by examiner

*Primary Examiner*—Karl Group
(74) *Attorney, Agent, or Firm*—Nison Peabody LLP

(57) ABSTRACT

Radio-opaque glass ceramics are described which have high chemical durability and adjustable translucency, brightness and coefficient of thermal expansion.

14 Claims, 8 Drawing Sheets

SEM IMAGE OF A GLASS CERAMIC COMPRISING SR-APATITE
AS THE MAIN CRYSTALLINE PHASE

SEM IMAGE OF A GLASS CERAMIC COMPRISING SR-APATITE
AS THE MAIN CRYSTALLINE PHASE AND $RbAlSi_2O_6$ AS A FURTHER CRYSTALLINE PHASE

SEM IMAGE OF A GLASS CERAMIC COMPRISING SR-APATITE
AS THE MAIN CRYSTALLINE PHASE AND POLLUCITE AS A FURTHER CRYSTALLINE PHASE

SEM IMAGE OF A GLASS CERAMIC COMPRISING SR-APATITE
AS THE MAIN CRYSTALLINE PHASE AND LEUCITE AS A FURTHER CRYSTALLINE PHASE

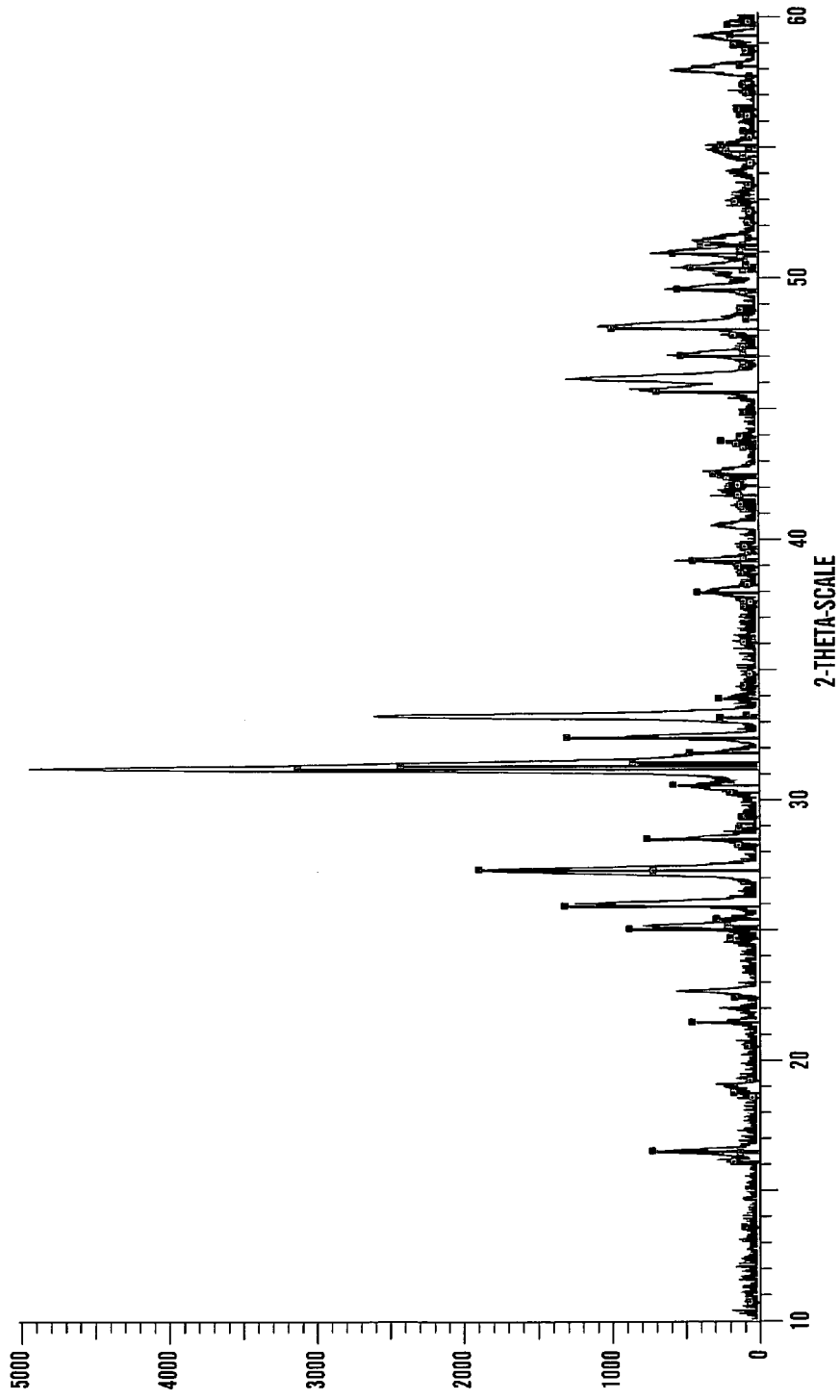

TRANSLUCENT AND RADIO-OPAQUE GLASS CERAMICS

The present application is division of U.S. patent application Ser. No. 10/932,245, filed Sep. 1, 2004 now U.S. Pat. No. 7,183,232, which claims priority to German Patent Application No. 103 40 597.6, filed Sep. 1, 2003, which are hereby incorporated by reference in their entirety.

The invention relates to translucent radio-opaque glass ceramics with high chemical durability and with adjustable translucency, brightness and coefficient of thermal expansion.

In the field of dentistry glass ceramics are commonly used for restorative dental prosthesis, for instance for producing inlays, onlays, crowns, bridges and veneers. DE 44 23 793 discloses phosphosilicate glass ceramics with improved optical properties, adjustable translucency and optical brightness. These materials contain leucite as a main crystalline phase and have the advantage that their optical properties closely match those of the natural teeth. While phosphate-free leucite glass ceramics usually contain pigments in order to adapt their appearance to that of the natural tooth, the phosphosilicate glass ceramics according to DE 44 23 793 do not require the addition of such components. Furthermore, the color brightness and color impression from the depth of the material surmounted that of other leucite materials by far.

The phosphosilicate glass ceramics of DE 44 23 793 contain calcium phosphate, the CaO-content is 2.5 to 11.5 wt %. In combination with $P_2O_5$ and F the CaO-content causes the formation of needle-shaped calcium apatite, $Ca_5(PO_4)_3F$, alongside with leucite, $KAlSi_2O_6$. A disadvantage of these materials is that they show only little or no radio-opacity.

Radio-opacity of biomaterials is important in clinical application since it allows to detect the preparation border of a metal free veneer or crown versus the natural teeth by X-ray examination. The detection of the preparation border is important in clinical aftercare and in detecting undesired secondary caries and is therefore an integral part in the attempt to preserve the natural teeth substance of the patient.

From U.S. Pat. No. 5,952,235 it is known that apatite crystal phases of very small dimensions and amounts can be formed in glasses, so that the products look like glasses and are transparent. These glasses can be used in optical systems. However, these materials are not useful for dental applications since they lack opacity and translucency.

WO 91/12212 describes an apatite glass ceramic containing relatively high amounts of CaO and $Al_2O_3$ and a relatively small amount of $SiO_2$. These materials exhibit a high degree of whiteness which renders them useful as glass ionomer cements. However, when using these materials as dental restorative materials they have the disadvantage that they are very opaque and that their translucency is not adjustable.

U.S. Pat. No. 5,236,495 discloses non-siliceous materials phosphate glass ceramics. These pure phosphate materials are unsatisfactory with regard to their chemical durability and are therefore not suitable as dental restorative materials.

The prior art materials show a couple of disadvantages and it is an object of the present invention to eliminate these disadvantages, i.e. to provide dental materials which are radio-opaque, have high chemical durability and adjustable translucency, brightness and coefficient of thermal expansion.

This object has surprisingly been achieved by glass ceramic which comprise:

| Component | Wt. % |
| --- | --- |
| $SiO_2$ | 46.0–58.0 |
| $P_2O_5$ | 2.0–6.0 |
| $Me_2O_3$ | 10.0–22.0 |
| $Me_2O$ | 14.5–30.0 |
| MeO | 4.0–13.0 |
| F | 0.3–3.0 | with $Me_2O_3$ being selected from:

| Component | Wt. % |
| --- | --- |
| $Al_2O_3$ | 8.0–16.0 |
| $Y_2O_3$ | 0.1–9.0 |
| $BO_3$ | 0–9.0 | with $Me_2O$ being selected from:

| Component | Wt. % |
| --- | --- |
| $Li_2O$ | 0–3.0 |
| $Na_2O$ | 0–9.0 |
| $K_2O$ | 3.0–14.0 |
| $Rb_2O$ | 0–12.5 |
| $Cs_2O$ | 0–18.0 | with MeO being selected from:

| Component | Wt. % |
| --- | --- |
| MgO | 0–9.0 |
| CaO | 0–2.5 |
| SrO | 0–13.0 | with the proviso that at least one of SrO or MgO$\geq$3.1 wt. % if CaO is 0.1 to 2.5 wt.-%.

The glass ceramic has apatite as a main crystalline phase.

In the glass ceramics of the invention $Me_2O_3$, $Me_2O$ and MeO are each selected from the compounds specified above. For instance, MeO may be a singe compound such as 13 wt. % SrO or a mixture of compounds such as 9 wt. % MgO and 4 wt. % SrO.

For the components exist the following preferred values which can be chosen independently of one another:

| Component | Wt. % |
| --- | --- |
| $SiO_2$ | 46.5–58.0 |
| $P_2O_5$ | 2.2–6.0 |
| $Me_2O_3$ | 11.0–21.9 |
| $Me_2O$ | 14.6–29.0 |
| MeO | 5.0–13.0 |
| F | 0.4–3.0 | for Me$_2$O$_3$:

| Component | Wt. % |
|---|---|
| Al$_2$O$_3$ | 9.4–16.0 |
| Y$_2$O$_3$ | 0.2–9.0 |
| B$_2$O$_3$ | 0.1–8.8 | for Me$_2$O:

| Component | Wt. % |
|---|---|
| Li$_2$O | 0–1.0 |
| Na$_2$O | 0–8.7 |
| K$_2$O | 3.2–13.0 |
| Rb$_2$O | 0–12.4 |
| Cs$_2$O | 0–17.8 | for MeO:

| Component | Wt. % |
|---|---|
| MgO | 0–8.5 |
| CaO | 0–2.4 |
| SrO | 3.6–13.0 |

For the components exist the following more preferred values which can also be chosen independently of one another:

| Component | Wt. % |
|---|---|
| SiO$_2$ | 47.0–57.8 |
| P$_2$O$_5$ | 2.4–6.0 |
| Me$_2$O$_3$ | 11.5–21.8 |
| Me$_2$O | 14.7–28.5 |
| MeO | 6.0–13.0 |
| F | 0.5–3.0 | for Me$_2$O$_3$:

| Component | Wt. % |
|---|---|
| Al$_2$O$_3$ | 11.0–15.9 |
| Y$_2$O$_3$ | 0.1–9.0 |
| B$_2$O$_3$ | 0.3–8.6 | for Me$_2$O:

| Component | Wt. % |
|---|---|
| Li$_2$O | 0–0.5 |
| Na$_2$O | 0.1–8.4 |
| K$_2$O | 3.4–12.0 |
| Rb$_2$O | 0–12.0 |
| Cs$_2$O | 0–17.6 | for MeO:

| Component | Wt. % |
|---|---|
| MgO | 1.0–8.0 |
| CaO | 1.0–2.4 |
| SrO | 4.0–11.0 |

The radio-opaque glass ceramic as described above can additionally comprise ZrO$_2$, TiO$_2$, CeO$_2$. Preferred ranges for these compounds, which can be chosen independently of one another, are as follows:

| Component | Wt. % |
|---|---|
| ZrO$_2$ | 0–1.0 |
| TiO$_2$ | 0–0.4 |
| CeO$_2$ | 0–1.0 |

The radio-opaque glass ceramic according to invention can further comprise one or more coloring or fluorescent metal oxides, selected from oxides of the group of metals consisting of Zr, Ta, Yb, Nb, Tb, La, Er, Pr, Ce, Ti, V, F, Mn and mixtures thereof. The total amount of these components is preferably less than 7% by weight, more preferably less than 5% by weight.

In the glass ceramic of the present invention apatite is the main crystalline phase. According to the present invention the term "apatite" is used for all crystal compositions which are crystallize in the apatite crystalline structure. According to one embodiment the apatite phase may be a pure Ca-apatite phase of the formula Ca$_5$(PO$_4$)$_3$F. According to a preferred embodiment of the invention the apatite phase is a phase of the formula Ca$_5$(PO$_4$)$_3$F wherein the Ca is totally or partially replaced by Sr and/or Mg. Even more preferred are apatite phases wherein up to 50% of the calcium ions are replaced by Sr$^{2+}$ and/or Mg$^{2+}$. In the following, apatite phases wherein Ca ions are replaced by Sr and/or Mg ions will also be referred to as apatite solid solutions, apatite solid solution phases or simply solid solutions. Preferred apatite solid solution phases are Sr$_{7.3}$Ca$_{2.7}$(PO$_4$)$_6$F$_2$, such as strontium fluorapatite, in particular Sr$_5$(PO$_4$)$_3$F.

It is further preferred that the crystals of the main crystal phase are needle shaped, crystal apatite phases having the form of needles with an average length of 0.1 to less than 10 μm are particularly preferred.

In addition to the main crystal phase the glass ceramics of the present invention preferably also contain one or more, in particular 1 to 3, further crystalline phases. In a particularly preferred embodiment the radio-opaque glass ceramic of the present invention has as a further crystalline phase KAlSi$_2$O$_6$, RbAlSi$_2$O$_6$ and/or CsAlSi$_2$O$_6$. A characterization/definition of KAlSi$_2$O$_6$ (leucite) can be found in JCPDS 38-1423, of RbAlSi$_2$O$_6$ (Rb-leucite) in JCPDS 85-1627 and of CsAlSi$_2$O$_6$ (pollucite) in JCPDS 88-0056. Such additional crystal phases are preferably of tetragonal or cubic modification.

The glass ceramics according to the invention show an opacity which greatly resembles the opacity of the natural tooth. Preferably the ceramics have a opacity of about 0.3 to 0.7 (according to BS 512-1978) because it gives dental restorations a natural appearance and very good aesthetic properties.

In addition the glass ceramics of the invention have a high radio-opacity. The radio-opacity of dental materials is usually given as percentage of the a radio-opacity an aluminum plate having a thickness of 1 mm. The glass ceramics of the invention preferably have a radio-opacity of at least 100% Al, i.e. a glass ceramic plate with a thickness of 1 mm shows at least the same radio-opacity as a 1 mm aluminum plate. More preferably the radio-opaque glass ceramic of the present invention have a radio-opacity of more than 200%, even more preferably of more than 250% and most preferably of more than 300% of the radio-opacity of a 1 mm Al plate (200% Al, 250% Al, 300% Al). By incorporation of cations having large ion radii, i.e. a covalent radius of app. about 1.6 Å, and relatively high atom masses, i.e. atomic masses of at least 85, it is possible to increase the radio-opacity.

A radio-opaque glass ceramic as described above wherein at least one of crystals of the main phase and at least one of the crystals of the secondary phase form a second phase is a preferred embodiment of the present invention.

FIG. 8 shows the X-ray diffraction pattern of the glass ceramic of FIG. 7.

Figure 1:
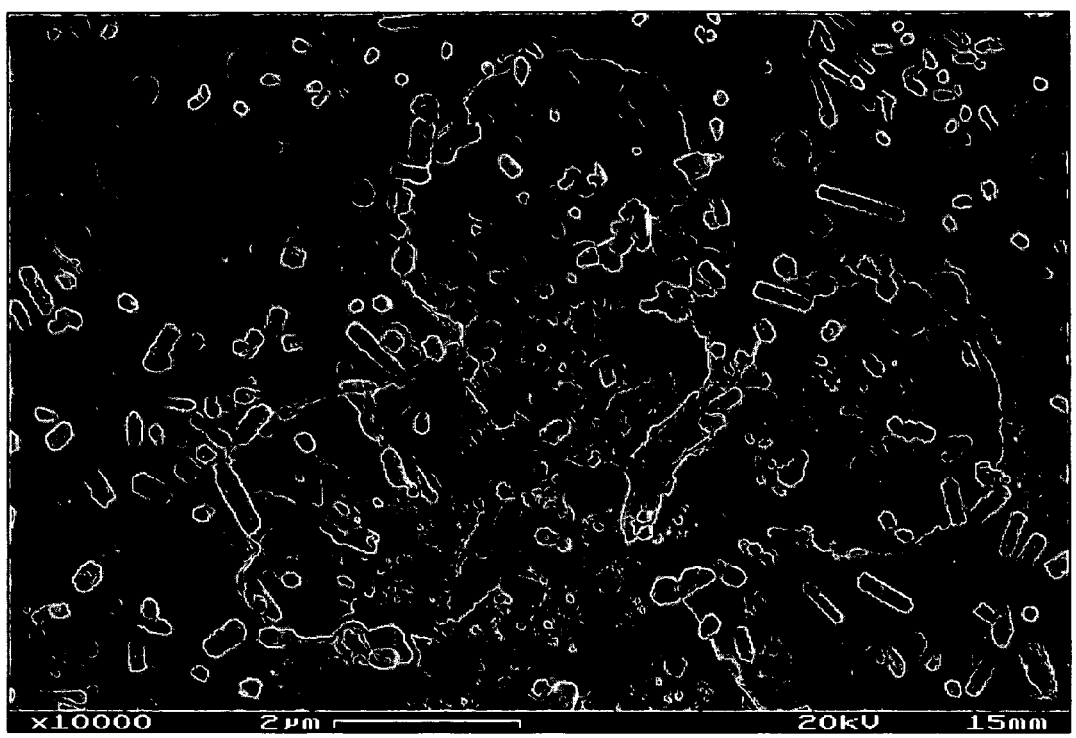
FIG. 1 is a SEM image of a glass ceramic according to the invention comprising Sr-apatite as the main crystalline phase (Example 1).
Figure 3:
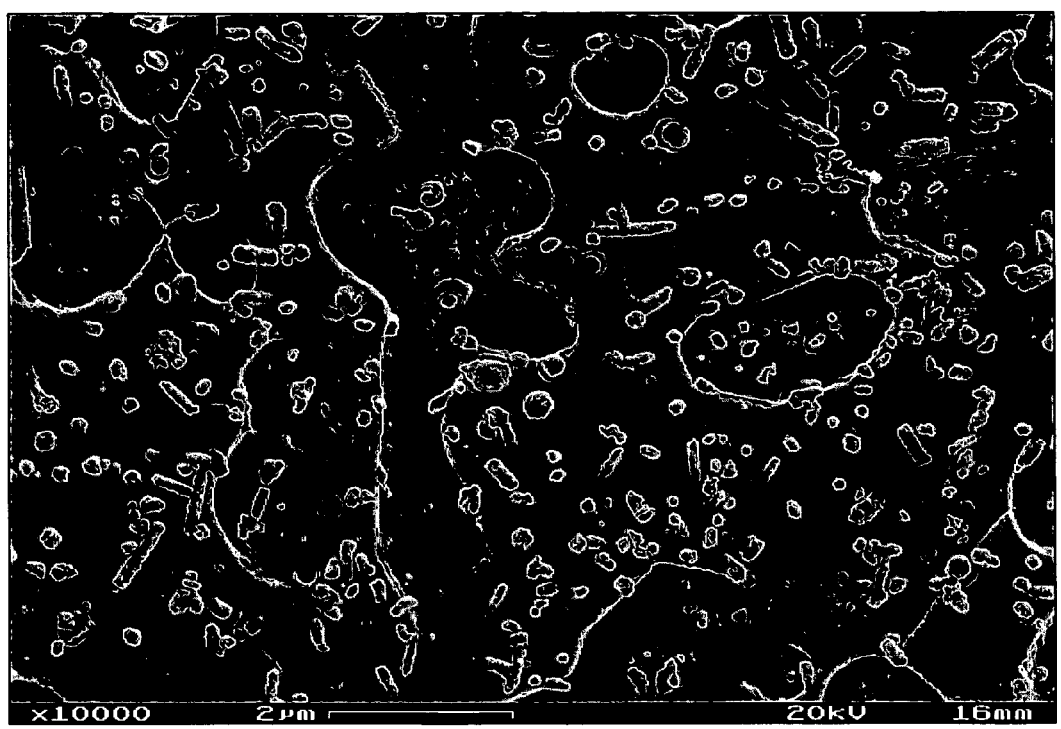
FIG. 3 is a SEM image of a glass ceramic according to the invention comprising Sr-apatite as the main crystalline phase and $RbAlSi_2O_6$ as a further crystalline phase (Example 8).
Figure 5:
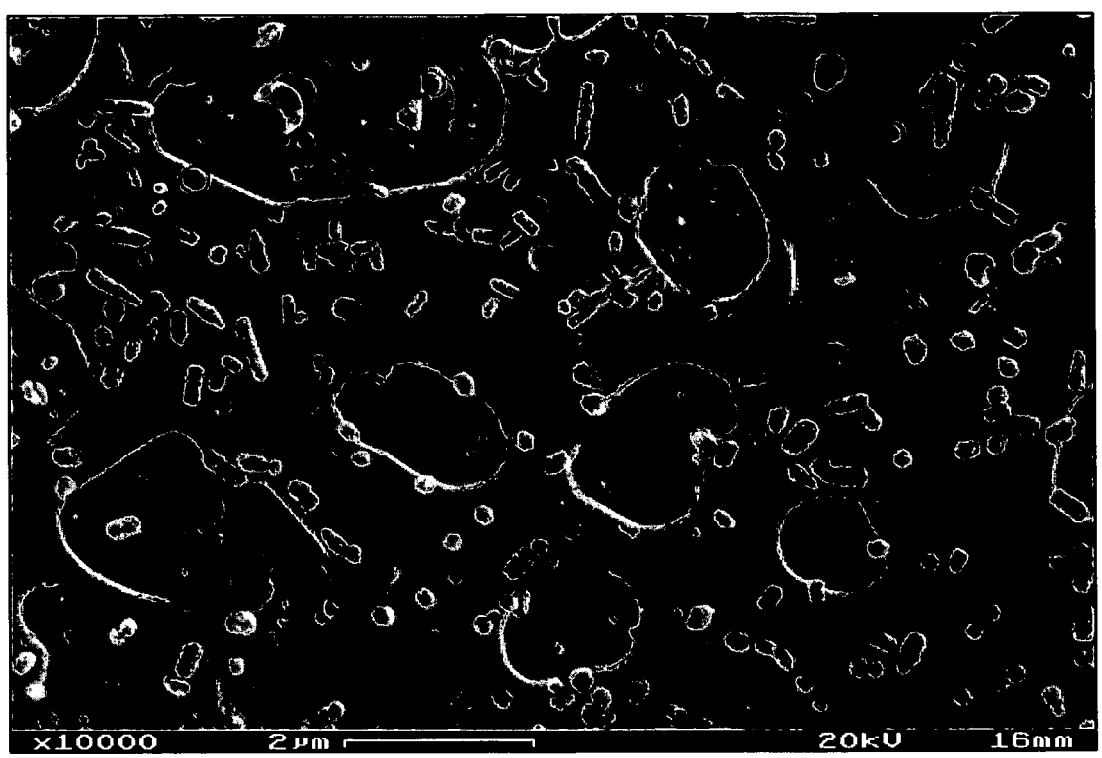
FIG. 5 is a SEM image of a glass ceramic according to the invention comprising Sr-apatite as the main crystalline phase and pollucite as a further crystalline phase (Example 19).
Figure 7:
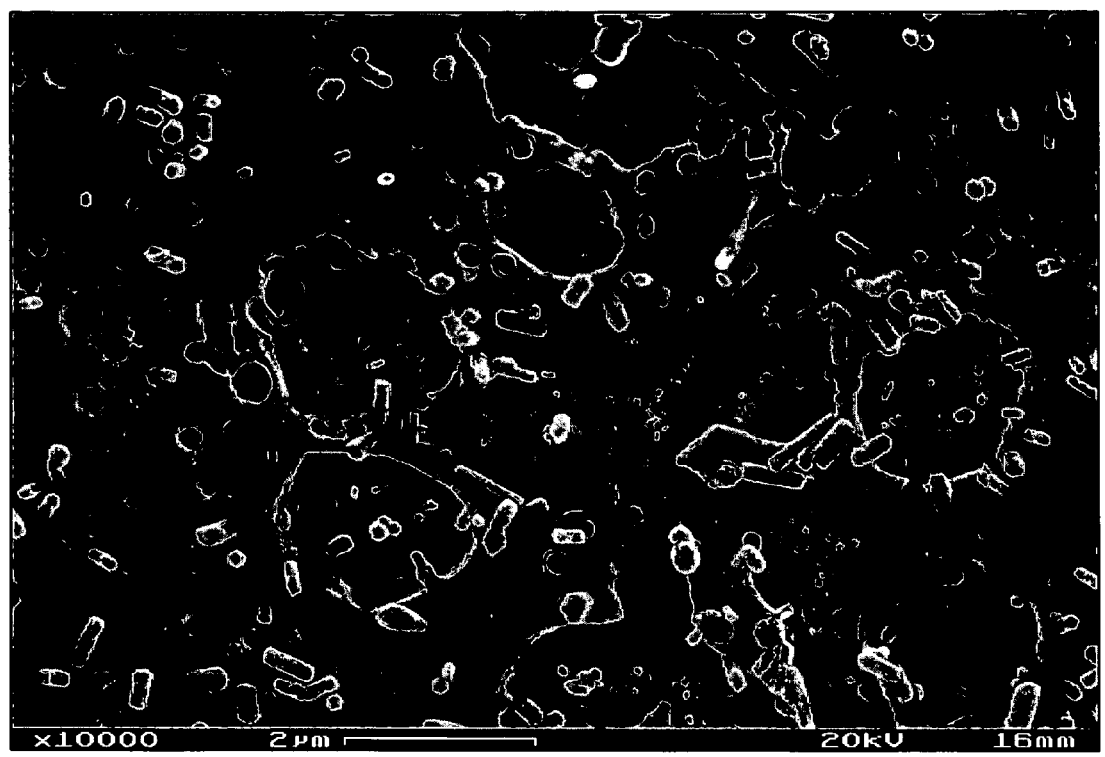
FIG. 7 is a SEM image of a glass ceramic according to the invention comprising Sr-apatite as the main crystalline phase and leucite as a further crystalline phase (Example 20).

In FIGS. 1, 3, 5 and 7 the main apatite phase forms needles. The secondary crystal phases are identifiable as etching patterns.

The leucite content of the glass ceramics according to the invention can be adjusted by varying the chemical composition of the starting glass, e.g. by varying the content of $K_2O$ and/or $Al_2O_3$. By varying the leucite content it is possible to tailor the coefficient of thermal expansion to the desired application of the glass ceramic. The coefficient of thermal expansion of the radio-opaque glass ceramics can also be increased by the presence of $RbAlSi_2O_6$ and/or pollucite as a further crystalline phase.

The coefficient of thermal expansion of the radio-opaque glass ceramics according to the present invention can be adapted to a wide range of substrates. Therefore the glass ceramics are suitable as facing materials for many different substrates including other ceramics, such as $ZrO_2$ and its composites, $Al_2O_3$ and its composites, glass ceramic materials, such as lithium silicate, metal alloys based on Ag—Au, Au, Au—Pt, Ag—Pd, Pd, Co—Cr, as well as Ti and its alloys.

The glass ceramics of the invention are particularly suitable for coating or facing dental alloys with high contents of gold which have coefficients of thermal expansion within a range of 12 to $16*10^{-6}$ $K^{-1}$.

The glass ceramics of the invention are also particularly suitable for coating or facing materials having coefficients of thermal expansion in the range of about 6 to $10*10^{-6}$ $K^{-1}$ such as $Al_2O_3$ or $ZrO_2$ ceramics or titanium and its alloys.

In the oral cavity dental materials are permanently subjected e.g. to acidic liquids. The chemical durability of the materials is therefore another significant aspect. It is of utmost importance that ceramics used for dental purposes do not loose their brightness and roughness during use because otherwise they would invite plaque formation to occur. The radio-opaque glass ceramics of the present invention are characterized by high chemical stability. The ceramics preferably have a solubility value of less than 70.0 μg/cm², measured according to ISO 6872; 1995, and more preferably of less than 50.0 μg/cm². It was surprisingly found that the chemical durability can be increased by the presence of $Y_2O_3$ and, therefore, $Y_2O_3$ containing ceramics are particularly preferred.

The radio-opaque glass ceramics according to the invention preferably have the form of a powder, a blank or a block. A particularly preferred embodiment of the present invention is a radio-opaque glass ceramic as defined above which has the shape of a dental restoration and it is most preferred that the dental restoration is an inlay, an onlay, a bridge, an abutment, a veneer, a facet, a crown, a partial crown, a framework or a coping.

The glass ceramics of the present invention are also suitable for the preparation of other glasses or glass ceramics. Glasses or glass ceramics which comprise a radio-opaque glass ceramic according to the invention form another aspect of the present invention. The radio-opaque glass ceramic according to the present invention can be combined with a wide variety of other glasses and/or glass ceramics. Such mixtures are also referred to as inorganic-inorganic composites.

Glasses and glass ceramics which can preferably be combined with the class ceramics of the present invention are disclosed in DE 43 14 817, DE 44 23 793, DE 44 23 794, DE 44 28 839, DE 196 47 739, DE 197 25 552 and DE 100 31 431. These glasses and glass ceramics are derived from silicate or borate or phosphate or alumina silicate systems. Preferred glasses and glass ceramics are derivable from the systems $SiO_2$—$Al_2O_3$—$K_2O$ (with cubic or tetragonal leucite crystals), $SiO_2$—$B_2O_3$—$Na_2O$, alkali-silicate, alkali-zinc-silicate, silico-phosphate and/or $SiO_2$—$ZrO_2$.

Particularly preferred glasses and glass ceramics for combining with the glass ceramics of the present invention are defined as follows:

Low-temperature-sintering potassium-zinc-silicate glass (DE 100 31 431):

| Component | Amount (in wt. -%) |
|---|---|
| $SiO_2$ | 60.0–72.0 |
| $Li_2O$ | 1.0–5.0 |
| $K_2O$ | 10.0–23.0 |
| ZnO | 8.5–20.0 |

Low temperature-sintering apatite glass ceramic (DE 100 31 430):

| Component | Amount (in wt. -%) |
|---|---|
| $SiO_2$ | 56.0–65.0 |
| $Li_2O$ | 1.8–5.3 |
| $K_2O$ | 9.0–17.5 |
| ZnO | 9.0–16.0 |
| CaO | 3.5–10.5 |
| $P_2O_5$ | 2.0–6.0 |
| F | 0.5–1.0 |

Translucent apatite glass ceramic (DE 197 25 555/DE 197 25 553):

| Component | Amount (in wt. -%) |
|---|---|
| $SiO_2$ | 45.0–70.0 |
| $Al_2O_3$ | 5.0–22.0 |
| $K_2O$ | 3.0–8.5 |
| $Na_2O$ | 4.0–13.0 |
| CaO | 1.5–11.0 |
| $P_2O_5$ | 0.5–6.5 |
| F | 0.1–2.5 |

Alkali silicate glass (DE 197 25 552):

| Component | Amount (in wt. -%) |
|---|---|
| $SiO_2$ | 55.0–71.0 |
| $Al_2O_3$ | 5.0–16.0 |
| $B_2O_3$ | 0.2–10.0 |
| $K_2O$ | 4.5–10.0 |
| $Na_2O$ | 3.0–14.0 |

Sinterable lithium disilicate glass ceramic (DE 196 47 739):

| Component | Amount (in wt. -%) |
|---|---|
| $SiO_2$ | 57.0–80.0 |
| $Al_2O_3$ | 3.0–5.0 |
| $La_2O_3$ | 0.1–6.0 |
| $Li_2O$ | 11.0–19.0 |

Alkali-zinc-silicate glass-ceramics and glasses (DE 44 28 839):

| Component | Amount (in wt. -%) |
|---|---|
| $SiO_2$ | 52.0–63.5 |
| $Me^{III}_2O_3$ | 8.5–13.0 |
| $Na_2O$ | 1.5–20.0 |
| ZnO | 2.0–8.0 |
| $Me^{II}O$ | 2.5–6.5 |
| $TiO_2 + ZrO_2$ | 0.5–6.0 |

$ZrO_2$—$SiO_2$— Glaskeramik (DE 44 23 794):

| Component | Amount (in wt. -%) |
|---|---|
| $SiO_2$ | 42.5–58.5 |
| $Li_2O$ | 7.0–14.5 |
| $P_2O_5$ | 4.0–13.5 |
| $ZrO_2$ | 15.0–28.0 |

Leucite—containing phosphosilicate glass ceramic (DE 44 23 793):

| Component | Amount (in wt. -%) |
|---|---|
| $SiO_2$ | 49.0–57.5 |
| $Al_2O_3$ | 11.4–21.0 |
| $P_2O_5$ | 0.5–5.5 |
| CaO | 2.5–11.5 |
| $K_2O$ | 9.0–22.5 |
| $Na_2O$ | 1.0–9.5 |
| $ZrO_2$ | 0.8–8.5 |
| F | 0.25–2.5 |

Opalescent glass (DE 43 14 817):

| Component | Amount (in wt. -%) |
|---|---|
| $SiO_2$ | 48.0–66.0 |
| $Me^{III}_2O_3$ | 5.0–20.0 |
| $Me^{I}_2O$ | 6.0–22.0 |
| $Me^{II}O$ | 3.5–16.0 |
| $Me^{IV}O_2$ | 0.5–10.0 |
| $P_2O_5$ | 0.5–5.0 |

Preferably 20 to 80 wt. % of one ore more radio-opaque glass ceramic according to the invention are mixed with 80 to 20 wt. % of one or more of the above defined glasses or glass ceramics. By mixing such glasses with the radio-opaque glass ceramic according to the invention the coefficient of thermal expansion can be adjusted in a range of from 6 to $20*10^{-6}$ $K^{-1}$. Glasses and glass ceramics which are obtained by mixing one ore more radio-opaque glass ceramics according to the invention with one ore more other glasses or glass ceramics are also included in the present invention. The composition of these mixed glasses and glass ceramics can be calculated from the composition of the glasses and/or glass ceramics used for preparing the mixture and their percentages. These mixed glasses and glass ceramics are characterized by the presence of the apatite crystalline phase of the radio-opaque glass ceramics of the invention. According to the present invention glasses and glass ceramics which are free of BaO are preferred.

The development of the radio-opaque glass ceramic according to the present invention is based on the knowledge of the fundamental principles of controlled crystallization to give glass ceramics. The starting point is the controlled nucleation by phase separation which is based on a glass in glass phosphate phase separation.

It was surprisingly found that the process of the invention proceeds in such a way that the preferred ions, such as $Sr^{2+}$-ions in CaO-free compositions or in compositions with small amounts of CaO, are enriched in the droplet phase. Until now the phenomenon of apatite formation in glass ceramics was only known for glasses having a content of CaO of at least 2.5 wt. %.

Figure 2:
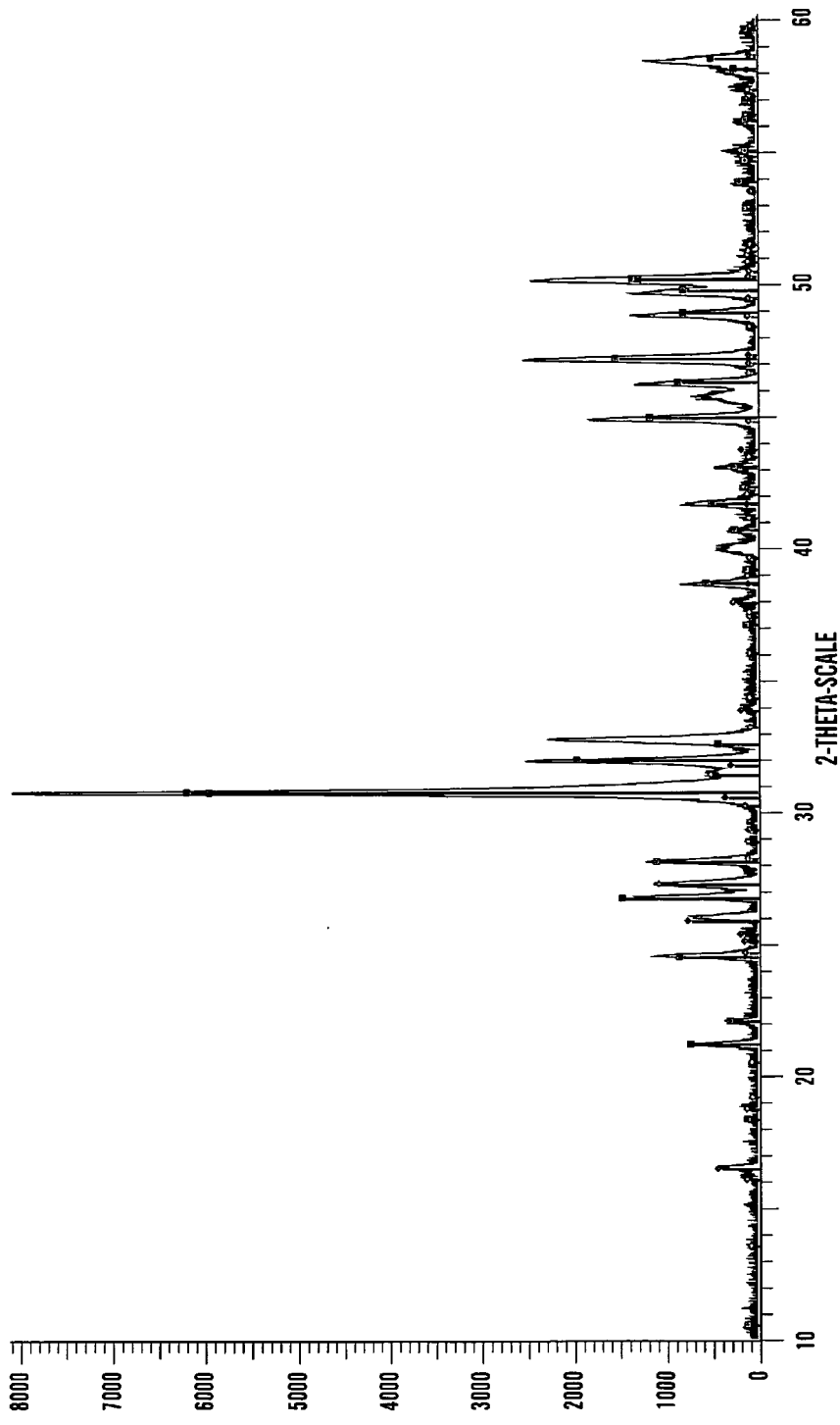
FIG. 2 shows the X-ray diffraction pattern of the glass ceramic of FIG. 1.
Figure 4:
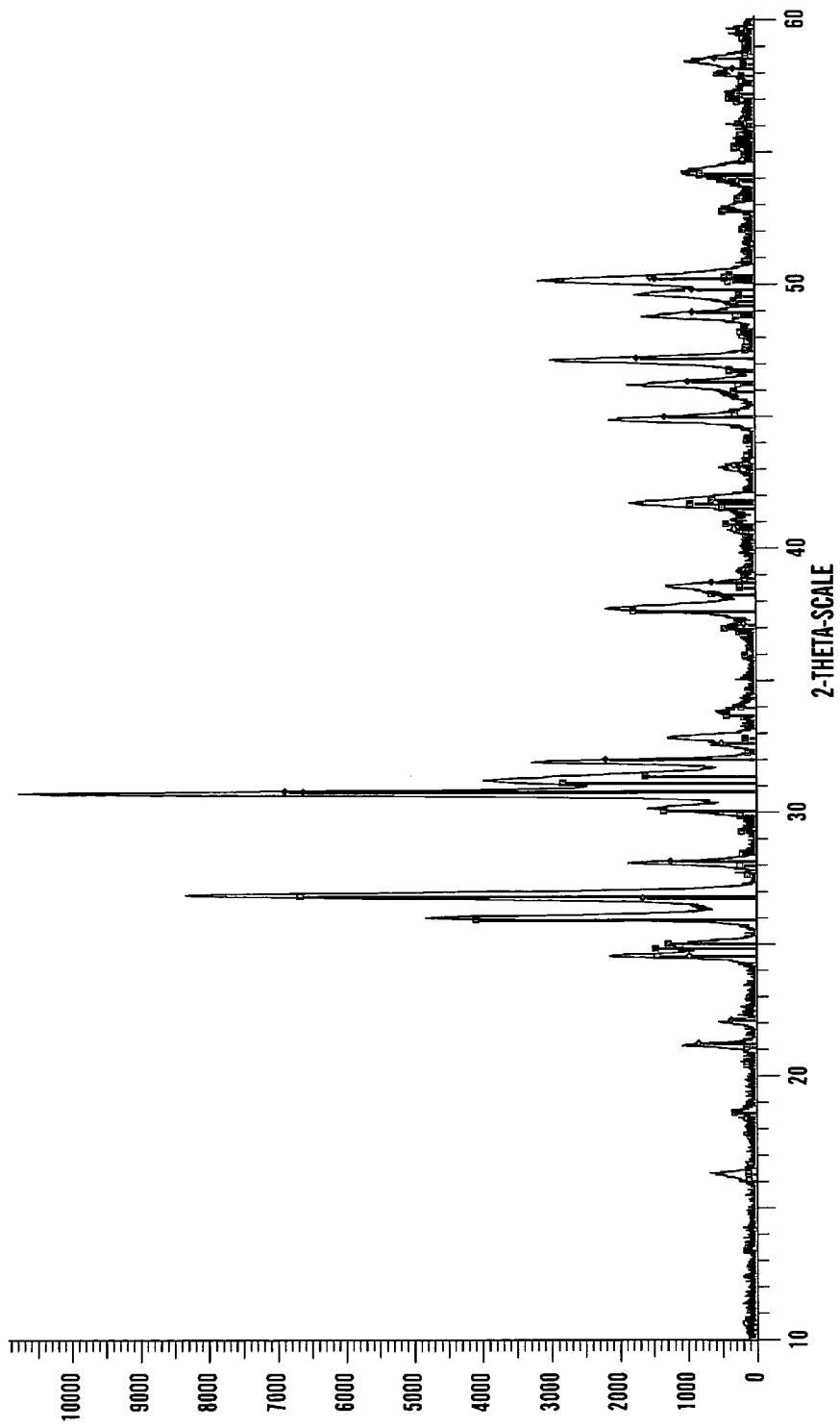
FIG. 4 shows the X-ray diffraction pattern of the glass ceramic of FIG. 3.
Figure 6:
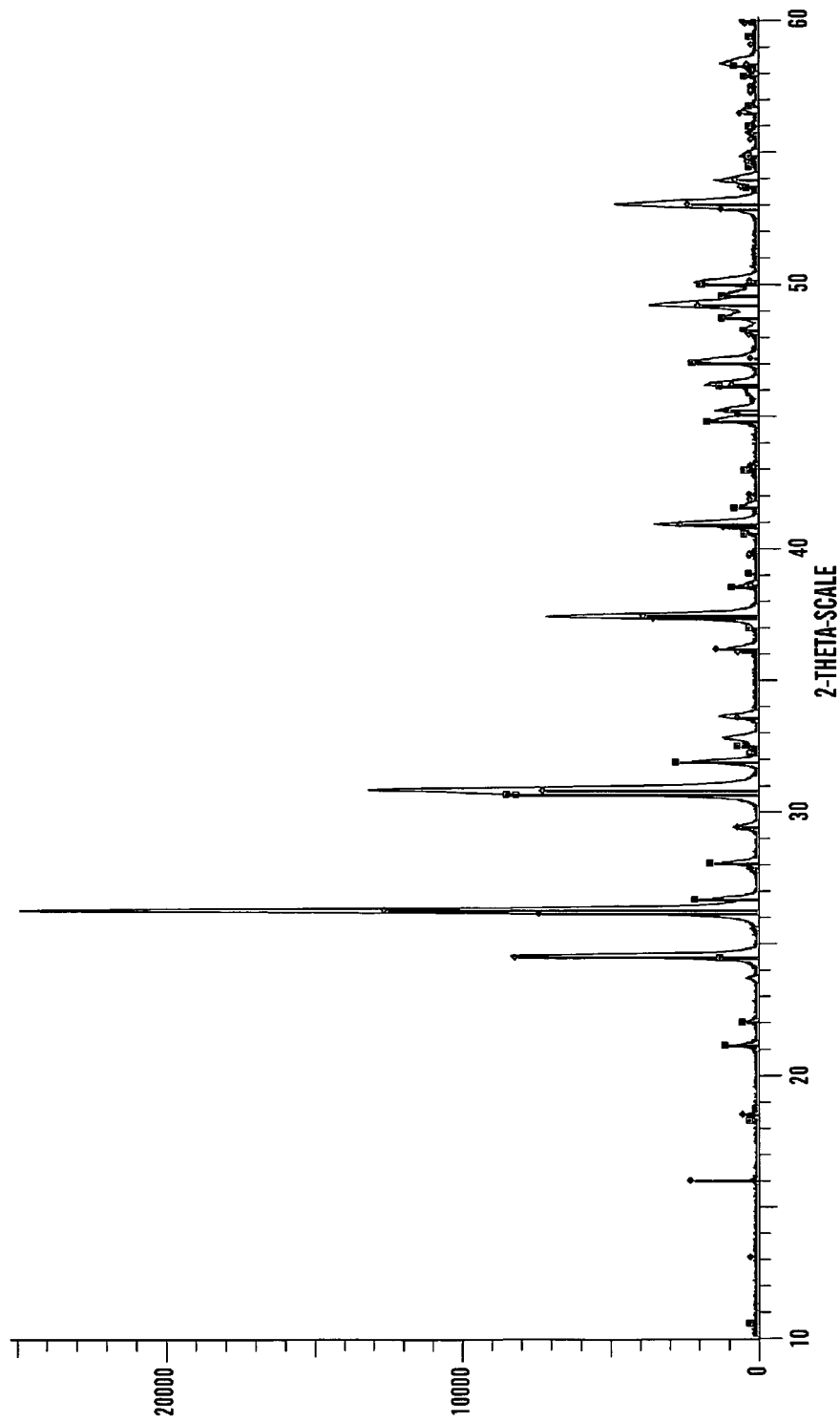
FIG. 6 shows the X-ray diffraction pattern of the glass ceramic of FIG. 5.

In addition to that it was surprisingly found that $Sr^{2+}$-ions alone or in combination with small amounts of $Ca^{2+}$ lead to the formation of apatite nuclei in the droplet phase, the phase which is separated from the glass phase. This is often called as a phase separation phenomenon. The thermal treatment as described below results in a controlled crystallization of the phase-separated glasses and apatite or apatite solid solution are obtained that grow in needle-shaped form. The formation of such apatites was verified by scanning electron microscopy (SEM). The verification of the exact crystallographic assignment was achieved by XRD. The micro structure is exemplarily shown in FIGS. 1, 3, 5 and 7, FIGS. 2, 4, 6 and 8 show XRD patterns of the glass ceramics shown in FIGS. 1, 3, 5 and 7.

Another aspect of the present invention is a process for the preparation of the radio-opaque glass ceramic as described above, which comprises (a) producing a melt of a starting glass containing the components of the glass ceramic, preferably at temperatures of 1200 to 1650° C., more preferably between 1500 to 1550° C., (b) pouring the melt of the starting glass into water to give glass granules, (c) optionally milling said glass granules to give a glass powder having a mean particle size of 1 to 500 µm, preferably less than 150 µm, (d) subjecting said glass granules of step (b) or said glass powder of step (c) to a heat treatment at a temperature of 700 to 1200° C., preferably at a temperature of 800 to 1100° C. for a period of 30 minutes to 6 hours, preferably 30 min. to 3 hours thus forming the radio-opaque glass ceramic of the invention.

In step (a) the components needed to form the glass ceramic, such as e.g. carbonates, oxides, fluorides, and phosphates, are homogeneously mixed. Then the mixture is heated to a temperature within the range that is given above in order to form a melt of the starting glass.

Subsequently in step (b) the glass melt of step (a) is poured into water. By this so-called fritting step glass granules are formed. By pouring the melted mixture into water small glass granules are obtained. Glass granules having a size within a range of 0.1 µm to <500 µm, in particular 0.1 µm to <150 µm are preferred.

In step (c) the glass granules are optionally milled. Usually they are grinded using standard mills to the desired particle size. The thus obtained glass powder preferably has a number average particle size of 1 to 500 µm, preferably less 200 µm and most preferably less than 100 µm.

In step (d) which follows step (b) or (c) the glass granules or glass powder is subjected to a thermal treatment in one or more steps at temperatures of 700 to 1200° C., preferably 800 to 1100° C., for a period of 30 minutes to 6 hours, preferably 30 minutes to 3 hours. The temperature should be higher than 800° C. in order to accelerate the formation of apatite crystals. The process of crystal growth takes place during step (d).

By SEM and XRD measurements it is possible to observe the apatite and apatite solid solutions as the main crystal phase. The size of the crystals can be adjusted by different heat treatments, i.e. one, two or more steps of heat treatment at different temperatures and different periods of time. In addition to the surprising finding of apatite and apatite solid solutions it was likewise found that by variation of the chemical composition within the above defined ranges and the use of different crystallization mechanisms a second crystalline phase, i.e. tetragonal leucite, Rb-leucite or Cs-leucite can be precipitated.

By incorporation of small amounts of $Ca^{2+}$ in combination with $Sr^{2+}$ apatite solid solutions were formed. Also when using samples which contained magnesium, apatite needles were formed when small amounts of $Ca^{2+}$ were present. By using the mechanism of controlled twofold crystallization (this means that both apatite and a second crystal phase like leucite crystallizes) a second crystalline phase was formed. This is due to a volume crystallization of the apatite in combination with a surface crystallization of the second phase. Thereby new combinations of properties of bio-materials are obtained, which are described in more detail in the experimental part.

The use of the radio-opaque glass ceramic as described above as a component of a glass or glass ceramic result in the formation of different micro structures. Such solid solution compositions are another aspect of the present invention. The main objective is to develop inorganic-inorganic composites with the radio-opaque glass ceramics according to the invention. Varying the part of the radio-opaque glass ceramic within that composite allows to adjust properties, such as the coefficient of thermal expansion and optical properties, e.g. the translucency.

The translucent and radio-opaque glass ceramic according to the invention is especially useful as a powder, resulting from step (d) of the above described manufacturing process. These powders can be used as such or in admixture with other glass or glass ceramic powders for coating different substrates as described before. This technique is characterized by applying a powder slurry or a wet powder material onto a substrate followed by a sintering step in order to fix the coating material to the substrate.

The radio-opaque glass ceramic powders according to the invention can also be used as a filler in organic-inorganic composite materials together with organic polymerizable monomers and an initiator system for the polymerization. The glass ceramic powder of the invention can be used as the sole filler or in combination with other filler components: When used as filler for organic-inorganic composites the glass ceramic powders of the invention preferably have a particle size of 0.1 µm to less than 250 µm, more preferably 0.1 µm to less than 10 µm. The glass ceramic powder is preferably used together with other filler types, such as rheological modifier.

The glass ceramic powder of the invention is also useful, alone or in admixture with the above specified other glasses or glass ceramic powders, for pressing a blank which is sintered to form the crystalline structure. These blanks have typically a circular or a rectangular cross-section with different length or heights. These blanks can be further processed to shaped products. The overall dimensions of such a blank are preferably adapted to the manufacture of dental restorations.

The formation of crystalline structures is preferably achieved by a two-stage process. In the first step surface crystallization takes place which is followed by the volume crystallization. However, it is also possible to terminate this process after the first step such that only surface crystallization will take place. This stage of an incomplete crystallization leads to lower mechanical strength and thus blanks which are easier to further process in following manufacturing procedures are obtained.

Alternatively, blanks can produced by pouring the glass melt of step (a) of the above process into a mould. The cast is then maintained at temperature of about 800 to 1100° C. to achieve crystallization. By controlling time and temperature it is possible to cause the formation of different crystal phases.

The use of a blank produced as described above in pressing processes is described in EP 915 625 B1.

The use of a block as described above in CAD/CAM-processes is still another preferred embodiment of the present invention.

The present invention is also directed to radio-opaque glass ceramic products which are obtainable by the process as described above and in particular to radio-opaque glass ceramic products which are in the form of a dental restoration. Preferred dental restorations which can be produced from the radio-opaque glass ceramics according to the invention are inlays, onlays, crowns, bridges, partial crowns, a veneers, copings, abutments, facings, frameworks or facets.

The invention is explained in more detail on the basis of the following examples.

EXAMPLES

Examples 1 to 30

Radio-Opaque Glass Ceramic

A total of 30 different radio-opaque glass ceramics according to the invention was produced as described above.

The composition of the 30 samples is given in Table I, together with the main crystal phases, which were analyzed via XRD (X-ray diffraction). $Sr_5(PO_4)_3F$ is strontium apatite phase (JCPDS 50-1744) and $Sr_{7.3}Ca_{2.7}(PO_4)_6F_2$ is Sr—Ca-mixed apatite phase (JCPDS 78-1715).

Samples of the different materials were examined after the heat treatment and cooling to room temperature with a Bruker-AXS diffractometer D 5005 operating with a Cu anode. The coefficient of thermal expansion was measured with the Bähr dilatometer.

TABLE I

Compositions and Main Crystalline Phases of Glass Ceramics

| Component | 1 wt. -% | 2 wt. -% | 3 wt. -% | 4 wt. -% | 5 wt. -% | 6 wt. -% | 7 wt. -% | 8 wt. -% |
|---|---|---|---|---|---|---|---|---|
| $SiO_2$ | 52.3 | 51.9 | 51.4 | 50.8 | 49.2 | 49.1 | 47.7 | 48.6 |
| $P_2O_5$ | 3.8 | 3.8 | 3.8 | 3.7 | 3.6 | 3.6 | 3.5 | 3.6 |
| $B_2O_3$ | 0.3 | 0.3 | 0.3 | 0.3 | 0.3 | 3.0 | 0.3 | 0.3 |
| $Al_2O_3$ | 13.6 | 13.5 | 13.3 | 13.2 | 12.8 | 12.7 | 12.4 | 12.8 |
| $Y_2O_3$ | 0.1 | 1.0 | 1.9 | 3.1 | 6.1 | 6.1 | 9.0 | 0.5 |
| $ZrO_2$ | 0.9 | 0.9 | 0.9 | 0.8 | 0.8 | 0.8 | 0.8 | 0.8 |
| $TiO_2$ | 0.2 | 0.2 | 0.2 | 0.2 | 0.2 | 0.2 | 0.2 | 0.2 |
| $CeO_2$ | 0.7 | 0.7 | 0.7 | 0.7 | 0.7 | 0.7 | 0.7 | 0.7 |
| $Li_2O$ | 0.2 | 0.2 | 0.2 | 0.2 | 0.2 | 0.2 | 0.2 | 0.2 |
| $Na_2O$ | 8.1 | 8.0 | 7.9 | 7.8 | 7.6 | 5.0 | 7.4 | 7.6 |
| $K_2O$ | 10.3 | 10.2 | 10.1 | 10.0 | 9.7 | 9.6 | 9.4 | 3.4 |
| $Rb_2O$ | — | — | — | — | — | — | — | 12.4 |
| $Cs_2O$ | — | — | — | — | — | — | — | — |
| MgO | — | — | — | — | — | — | — | — |
| CaO | — | — | — | — | — | — | — | — |
| SrO | 8.8 | 8.7 | 8.6 | 8.5 | 8.3 | 8.3 | 8.0 | 8.3 |
| F | 0.7 | 0.7 | 0.7 | 0.7 | 0.6 | 0.6 | 0.6 | 0.6 |
| main crystal phases | Sr-apatite leucite | Sr-apatite leucite | Sr-apatite leucite | Sr-apatite leucite | Sr-apatite leucite | Sr-apatite leucite | Sr-apatite leucite | Sr-apatite $RbAlSi_2O_6$ |

| Component | 9 wt. -% | 10 wt. -% | 11 wt. -% | 12 wt. -% | 13 wt. -% | 14 wt. -% | 15 wt. -% | 16 wt. -% |
|---|---|---|---|---|---|---|---|---|
| $SiO_2$ | 51.8 | 51.8 | 51.7 | 51.8 | 51.8 | 51.4 | 53.6 | 50.5 |
| $P_2O_5$ | 3.8 | 3.8 | 3.8 | 3.8 | 3.8 | 3.8 | 4.5 | 3.7 |
| $B_2O_3$ | 0.3 | 0.3 | 0.3 | 0.3 | 0.3 | 0.3 | 0.3 | 0.3 |
| $Al_2O_3$ | 13.6 | 13.6 | 13.5 | 13.6 | 13.6 | 13.6 | 12.9 | 14.0 |
| $Y_2O_3$ | 0.5 | 0.5 | 0.5 | 0.5 | 0.5 | 0.5 | 0.5 | 0.5 |
| $ZrO_2$ | 0.9 | 0.9 | 0.9 | 0.9 | 0.9 | 0.9 | 0.8 | 0.8 |
| $TiO_2$ | 0.2 | 0.2 | 0.2 | 0.2 | 0.2 | 0.2 | 0.2 | 0.2 |
| $CeO_2$ | 0.7 | 0.7 | 0.7 | 0.7 | 0.7 | 0.7 | 0.7 | 0.7 |
| $Li_2O$ | 0.2 | 0.2 | 0.2 | 0.2 | 0.2 | 0.2 | 0.2 | 0.2 |
| $Na_2O$ | 8.1 | 8.1 | 8.1 | 8.1 | 8.1 | 8.1 | 7.6 | 7.8 |
| $K_2O$ | 10.2 | 10.1 | 10.0 | 10.2 | 10.1 | 10.0 | 9.7 | 12.0 |
| $Rb_2O$ | — | — | — | 0.2 | 0.4 | 0.6 | — | — |
| $Cs_2O$ | 0.2 | 0.4 | 0.6 | — | — | — | — | — |
| MgO | — | — | — | — | — | — | — | — |
| CaO | — | — | — | — | — | — | — | — |
| SrO | 8.8 | 8.8 | 8.8 | 8.8 | 8.8 | 8.8 | 8.3 | 8.6 |
| F | 0.7 | 0.7 | 0.7 | 0.7 | 0.7 | 0.7 | 0.6 | 0.7 |
| main crystal phases | Sr-apatite leucite | Sr-apatite leucite | Sr-apatite leucite | Sr-apatite leucite | Sr-apatite leucite | Sr-apatite leucite | Sr-apatite leucite | Sr-apatite leucite |

TABLE I-continued

Compositions and Main Crystalline Phases of Glass Ceramics

| Component | 17 wt. -% | 18 wt. -% | 19 wt. -% | 20 wt. -% | 21 wt. -% | 22 wt. -% | 23 wt. -% | 24 wt. -% |
|---|---|---|---|---|---|---|---|---|
| $SiO_2$ | 52.7 | 49.5 | 45.7 | 53.0 | 49.5 | 48.3 | 53.2 | 57.3 |
| $P_2O_5$ | 2.5 | 3.7 | 3.4 | 3.9 | 3.9 | 3.8 | 3.9 | 3.4 |
| $B_2O_3$ | 0.3 | 0.3 | 0.3 | 0.3 | 8.4 | 8.2 | — | 0.3 |
| $Al_2O_3$ | 13.8 | 13.0 | 12.0 | 13.9 | 11.1 | 11.6 | 13.9 | 11.3 |
| $Y_2O_3$ | 0.5 | 0.5 | 0.5 | 0.5 | 0.5 | 0.5 | 0.5 | 0.5 |
| $ZrO_2$ | 0.9 | 0.8 | 0.8 | 0.9 | — | — | — | 0.8 |
| $TiO_2$ | 0.2 | 0.2 | 0.2 | 0.2 | — | — | — | 0.2 |
| $CeO_2$ | 0.7 | 0.7 | 0.7 | 0.8 | — | — | — | 0.7 |
| $Li_2O$ | 0.2 | 0.2 | 0.2 | 0.2 | — | — | — | 0.2 |
| $Na_2O$ | 8.2 | 7.7 | 7.1 | 8.3 | 7.5 | 6.9 | 8.3 | 7.8 |
| $K_2O$ | 10.4 | 9.8 | 3.2 | 10.5 | 11.4 | 11.2 | 10.5 | 9.1 |
| $Rb_2O$ | — | — | — | — | — | — | — | — |
| $Cs_2O$ | — | — | 17.6 | — | — | — | — | — |
| MgO | — | — | — | — | — | — | — | — |
| CaO | — | — | — | 2.4 | 2.4 | — | — | — |
| SrO | 8.9 | 13.0 | 7.8 | 4.5 | 4.6 | 8.8 | 9.0 | 7.8 |
| F | 0.7 | 0.6 | 0.6 | 0.7 | 0.7 | 0.7 | 0.7 | 0.6 |
| main crystal phases | Sr-apatite leucite | Sr-apatite leucite | Sr-apatite pollucite | SrCa-apatite leucite | $Sr_{7.3} Ca_{2.7}$-apatite | Sr-apatite | Sr-apatite leucite | Sr-apatite $NaSrPO_4$ |

| Component | 25 wt. -% | 26 wt. -% | 27 wt. -% | 28 wt. -% | 29 wt. -% | 30 wt. -% |
|---|---|---|---|---|---|---|
| $SiO_2$ | 49.6 | 50.2 | 49.0 | 52.0 | 50.7 | 48.8 |
| $P_2O_5$ | 6.0 | 3.7 | 3.6 | 3.8 | 3.9 | 4.0 |
| $B_2O_3$ | 0.3 | 0.3 | 7.9 | 0.3 | 0.3 | 0.3 |
| $Al_2O_3$ | 12.9 | 15.9 | 12.8 | 13.6 | 13.3 | 12.9 |
| $Y_2O_3$ | 0.5 | 0.5 | 0.5 | 4.0 | 4.0 | 4.1 |
| $ZrO_2$ | 0.8 | 0.9 | — | 0.9 | 0.9 | 0.9 |
| $TiO_2$ | 0.2 | 0.2 | — | 0.2 | 0.2 | 0.2 |
| $CeO_2$ | 0.7 | 0.7 | — | 0.8 | 0.8 | 0.8 |
| $Li_2O$ | 0.2 | 0.2 | — | 0.2 | 0.2 | 0.2 |
| $Na_2O$ | 7.7 | 3.4 | 7.6 | 8.0 | 7.9 | 7.5 |
| $K_2O$ | 9.7 | 14.3 | 9.7 | 10.2 | 10.0 | 9.5 |
| $Rb_2O$ | — | — | — | — | — | — |
| $Cs_2O$ | — | — | — | — | — | — |
| MgO | — | — | — | 3.1 | 5.0 | 8.0 |
| CaO | — | — | — | 2.2 | 2.1 | 2.1 |
| SrO | 8.4 | 8.6 | 8.3 | — | — | — |
| F | 3.0 | 0.7 | 0.6 | 0.7 | 0.7 | 0.7 |
| main crystal phases | Sr-apatite | Sr-apatite leucite | Sr-apatite | apatite leucite | apatite leucite | apatite leucite |

Example 31

Radioactivity of Radio-Opaque Glass Ceramics

The radioactivity of the composition of Example 1 and a powder of $SrCO_3$ as reference material were determined as follows:

30 to 40 g of powder of the samples were measured using a (gamma) spectrometer that was protected from background radiation. The detectors were calibrated by using a standard sand having the same geometry as the samples and being endowed with $^{152}Eu$. By using such a standard sand the (gamma) self-absorption within the sample can be accounted for.

Some decay products of the $^{238}U$- and $^{232}Th$-decay rows can be determined by (gamma)-spectroscopy. The activities of $^{238}U$ and $^{232}Th$ were calculated assuming radioactive equilibrium. The results are given in Table II. The calculation of the detection limit was performed according to DIN 25482.

As can be seen from the data of Table II, the use of $SrCO_3$ as raw material for the production of the glass ceramic is unobjectionable in regard of radioactivity. This is also true for the glass ceramic produced. The determination and calculation of the radioactivity of raw material and glass ceramic according to DIN 25482 showed that the values obtained were below the level of background radiation which is originating from the earth's crust and is about 0.03 $Bq*g^{-1}$ for $^{238}U$ and $^{232}Th$ respectively. According to ISO 6872 the limit for unsuitability for $^{238}U$-activity is 1.0 $Bq*g^{-1}$.

TABLE II

Radioactivity of the Glass Ceramic according to Example 1

| Component | Glass ceramic 1 wt. -% | raw material |
|---|---|---|
| $SiO_2$ | 52.3 | — |
| $P_2O_5$ | 3.8 | — |
| $B_2O_3$ | 0.3 | — |
| $Al_2O_3$ | 13.6 | — |
| $Y_2O_3$ | 0.5 | — |
| $ZrO_2$ | 0.9 | — |
| $TiO_2$ | 0.2 | — |
| $CeO_2$ | 0.7 | — |
| $Li_2O$ | 0.2 | — |
| $Na_2O$ | 8.1 | — |
| $K_2O$ | 10.3 | — |

TABLE II-continued

Radioactivity of the Glass Ceramic according to Example 1

| Component | Glass ceramic 1 wt. -% | raw material |
|---|---|---|
| $Rb_2O$ | — | — |
| $Cs_2O$ | — | — |
| MgO | — | — |
| CaO | — | — |
| SrO | 8.8 | 100% $SrCO_3$ |
| F | 0.7 | — |
| main crystal phases | Sr-apatite leucite | — |
| 238U / Bq * $g^{-1}$ | <0.03 | 0.036 ± 0.008 |
| 232Th / Bq * $g^{-1}$ | <0.03 | <0.03 |
| Tg/° C. | 518 | 561 |
| main crystal phases | Sr-apatite leucite | Sr-apatite leucite |

Examples 32 to 39

Thermal Expansion Coefficient of Radio-Opaque Glass Ceramics

To measure the coefficient of thermal expansion (alpha) a green body having the form of a bar was produced from a powder of the respective sample. Compositions according to examples 1 (32), 4 (33), 6 (34), 8 (35), 16 (36), 21 (37), 22 (38) and 26 (39) were used. The green bodies were sintered in a vacuum furnace, Furnace® P100 (Ivoclar Vivadent AG), using a heating rate of 60° C./min and a holding time of 1 min at the firing temperature as is given in Table III for the production of test pieces. Subsequently a glance firing was performed without vacuum, with a holding time of a 1 min at an end-temperature that was 20° C. above that of the preceding step. The coefficient of thermal expansion was that measured at the thus obtained test piece using a Bähr-dilatometer in the temperature range of 100 to 500° C. The coefficients of thermal expansion of eight samples are given in Table III.

Examples 40 to 47

Optical Properties of Radio-Opaque Glass Ceramics

Optical properties of glass ceramics were determined according to British Standard BS 5612;1978, sec. 8.11, by use of a Mi-nolta-CR 300 apparatus. The determined values have contrast values between 0 and 1 in comparison to a black and a white reference sample. The value zero represents 100% transmission and 1 represents 100% absorption. The optical properties of eight samples are given in Table III. As can be seen from the data in Table III the glass ceramics according to the invention can be used as opacifying material in dental applications since they are opaque.

Examples 48 to 55

Glass Transition Temperature of Radio-Opaque Glass Ceramics

The glass transition temperature was measured using a Bähr dilatometer or a differential scanning calorimetry (DSC) by Netsch. The results for the eight samples are given in Table III.

Examples 56 to 59

Chemical Durability of Radio-Opaque Glass Ceramics

To determine the chemical durability—which in the field of dental products mainly is stability against acid—sample bodies of four different radio-opaque glass ceramics having compositions according to examples 1 (56), 2 (57), 3 (58) and 4 (59) and having a diameter of 12 mm and a thickness of 1 mm were prepared. This preparation was achieved by sintering a glass ceramic powder having a particle size less than of 90 μm in a Programat® P100. The powder was kept at the sinter temperature for 1 min. The test pieces were then kept for 1 min at the temperatures which are given in Table III as the firing/sinter temperature. After cooling down to room temperature the chemical durability of the thus obtained test samples was determined according to ISO 6872:1995., i.e. as loss of mass after 16 h in 4% acetic acid at 80° C., and the obtained data are presented in Table IV.

As can be seen from the data of Table IV the chemical durability of the radio-opaque glass ceramics of the invention is good, i.e. it is by far better than the limit value for dental materials which according to ISO 6872:1995 is 100 μg*$cm^{-2}$. The data also show that the chemical durability can be improved by incorporating $Y_2O_3$ (see table IV). A high amount of $Y_2O_3$ corresponds to a high chemical durability.

TABLE III

Physical Properties of Glass Ceramics

| Component | 48 wt. -% | 49 wt. -% | 50 wt. -% | 51 wt. -% | 52 wt. -% | 53 wt. -% | 54 wt. -% | 55 wt. -% |
|---|---|---|---|---|---|---|---|---|
| $SiO_2$ | 51.9 | 50.8 | 49.1 | 48.6 | 50.5 | 49.5 | 48.3 | 50.2 |
| $P_2O_5$ | 3.8 | 3.7 | 3.6 | 3.6 | 3.7 | 3.9 | 3.8 | 3.7 |
| $B_2O_3$ | 0.3 | 0.3 | 3.0 | 0.3 | 0.3 | 8.4 | 8.2 | 0.3 |
| $Al_2O_3$ | 13.6 | 13.2 | 12.7 | 12.8 | 14.0 | 11.1 | 11.6 | 15.9 |
| $Y_2O_3$ | 0.5 | 3.1 | 6.1 | 0.5 | 0.5 | 0.5 | 0.5 | 0.5 |
| $ZrO_2$ | 0.9 | 0.8 | 0.8 | 0.8 | 0.8 | — | — | 0.9 |
| $TiO_2$ | 0.2 | 0.2 | 0.2 | 0.2 | 0.2 | — | — | 0.2 |
| $CeO_2$ | 0.7 | 0.7 | 0.7 | 0.7 | 0.7 | — | — | 0.7 |
| $Li_2O$ | 0.2 | 0.2 | 0.2 | 0.2 | 0.2 | — | — | 0.2 |
| $Na_2O$ | 8.1 | 7.8 | 5.0 | 7.8 | 7.8 | 7.5 | 6.9 | 3.4 |
| $K_2O$ | 10.3 | 10.0 | 9.6 | 8.4 | 12.0 | 11.4 | 11.2 | 14.3 |
| $Rb_2O$ | — | — | — | — | — | — | — | — |
| $Cs_2O$ | — | — | — | — | — | — | — | — |
| MgO | — | — | — | — | — | — | — | — |

TABLE III-continued

Physical Properties of Glass Ceramics

| Component | 48 wt. -% | 49 wt. -% | 50 wt. -% | 51 wt. -% | 52 wt. -% | 53 wt. -% | 54 wt. -% | 55 wt. -% |
|---|---|---|---|---|---|---|---|---|
| CaO | — | — | — | — | — | 2.5 | — | — |
| SrO | 8.8 | 8.5 | 8.3 | 8.3 | 8.6 | 4.8 | 8.8 | 8.6 |
| F | 0.7 | 0.7 | 0.6 | 0.6 | 0.7 | 0.7 | 0.7 | 0.7 |
| melting conditions | 1550° C./2 h | 1550° C./2 h | 1550° C./2 h | 1550° C./2 h | 1550° C./2 h | 1550° C./2 h | 1550° C./2 h | 1550° C./2 h |
| optical property after quenching | Opalescent | Opalescent | Opalescent | Opalescent | Opalescent | Opalescent | Opalescent | Opalescent |
| Heat treatment | 800° C./1 h and 1050° C. -/ 0.5 h | 800° C./1 h and. 1050° C./0.5 h | 800° C./1 h and 1050° C./0.5 h | 800° C./1 h and 1050° C. -/ 0.5 h | 800° C./1 h and 1050° C. -/ 0.5 h | 800° C./1 h and 1050° C. -/ 0.5 h | 800° C./1 h and 1050° C. -/ 0.5 h | 800° C./1 h and 1050° C. -/ 0.5 h |
| optical property after tempering | translucent | translucent light yellowish | Translucent light yellowish | Translucent | Translucent | Translucent | Translucent | translucent |
| firing temp./° C. | 920 | 980 | 990 | 1040 | 1080 | 860 | 860 | >1200 |
| C.T.E. * 100–500/$10^{-6}K^{-1}$ | 13.5 | 14.2 | 12.6 | 13.5 | 15.9 | 10.1 | 9.8 | 19.7 |
| Tg/° C. | 518 | 561 | 601 | 512 | 507 | 568 | 575 | 594 |
| main crystal phases | Sr-apatite leucite | Sr-apatite leucite | Sr-apatite leucite | Sr-apatite Rb-leucite | Sr-apatite leucite | Sr—Ca-apatite | Sr-apatite | Sr-apatite leucite |

* Coefficient of thermal expansion

TABLE IV

Chemical Durability of Glass Ceramics

| Component | 56 wt. -% | 57 wt. -% | 58 wt. -% | 59 wt. -% |
|---|---|---|---|---|
| $SiO_2$ | 52.3 | 51.9 | 51.4 | 50.8 |
| $P_2O_5$ | 3.8 | 3.8 | 3.8 | 3.7 |
| $B_2O_3$ | 0.3 | 0.3 | 0.3 | 0.3 |
| $Al_2O_3$ | 13.6 | 13.5 | 13.3 | 13.2 |
| $Y_2O_3$ | 0.1 | 1.0 | 1.9 | 3.1 |
| $ZrO_2$ | 0.9 | 0.9 | 0.9 | 0.8 |
| $TiO_2$ | 0.2 | 0.2 | 0.2 | 0.2 |
| $CeO_2$ | 0.7 | 0.7 | 0.7 | 0.7 |
| $Li_2O$ | 0.2 | 0.2 | 0.2 | 0.2 |
| $Na_2O$ | 8.1 | 8.0 | 7.9 | 7.8 |
| $K_2O$ | 10.3 | 10.2 | 10.1 | 10.0 |
| $Rb_2O$ | — | — | — | — |
| $Cs_2O$ | — | — | — | — |
| MgO | — | — | — | — |
| CaO | — | — | — | — |
| SrO | 8.8 | 8.7 | 8.6 | 8.5 |
| F | 0.7 | 0.7 | 0.7 | 0.7 |
| chemical durability / µg * $cm^{-2}$ | 67.0 | 57.8 | 37.1 | 24.1 |

Examples 60 to 64

Radio-Opacity of Radio-Opaque Glass Ceramics

The radio-opacity of the radio-opaque glass ceramics of the present invention was determined for five samples having compositions according to those of examples 5 (60), 7 (61), 8 (62), 16 (63) and 17 (64). The measurement of the radio-opacity was performed as follows:

According to the method of determining the radio-opacity of dental composite materials (ISO 4049) glass ceramic probes of 1 mm thickness were measured (device: Oralix DC by Gentix) and evaluated with Prepress RP 115 by Shamrock.

The reference for the value of radio-opacity is an aluminum-standard stair (Al 99.5%) of 1-5 mm thickness.

The results are summarized in Table V.

TABLE V

Radio-opacity of Glass Ceramics

| Component | 60 wt. -% | 61 wt. -% | 62 wt. -% | 63 wt. -% | 64 wt. -% |
|---|---|---|---|---|---|
| $SiO_2$ | 49.2 | 47.7 | 48.6 | 50.5 | 52.7 |
| $P_2O_5$ | 3.6 | 3.5 | 3.6 | 3.7 | 2.5 |
| $B_2O_3$ | 0.3 | 0.3 | 0.3 | 0.3 | 0.3 |
| $Al_2O_3$ | 12.8 | 12.4 | 12.8 | 14.0 | 13.8 |
| $Y_2O_3$ | 6.1 | 9.0 | 0.5 | 0.5 | 0.5 |
| $ZrO_2$ | 0.8 | 0.8 | 0.8 | 0.8 | 0.8 |
| $TiO_2$ | 0.2 | 0.2 | 0.2 | 0.2 | 0.2 |
| $CeO_2$ | 0.7 | 0.7 | 0.7 | 0.7 | 0.7 |
| $Li_2O$ | 0.2 | 0.2 | 0.2 | 0.2 | 0.2 |
| $Na_2O$ | 7.6 | 7.4 | 7.6 | 7.8 | 8.2 |
| $K_2O$ | 9.7 | 9.4 | 3.4 | 12.0 | 10.4 |
| $Rb_2O$ | — | — | 12.4 | — | — |
| $Cs_2O$ | — | — | — | — | — |
| MgO | — | — | — | — | — |
| CaO | — | — | — | — | — |
| SrO | 8.3 | 8.0 | 8.3 | 8.6 | 8.9 |
| F | 0.6 | 0.6 | 0.6 | 0.7 | 0.7 |
| radio-opacity (% Al) | 250 | 394 | 377 | 255 | 252 |

It can be seen from the data in Table V that the radio-opaque glass ceramics according to the invention exhibit values for the radio-opacity that are well above 100% Al.

Examples 65 to 74

Inorganic-Inorganic Composites Containing Radio-Opaque Glass Ceramics

Examples 65 to 74 demonstrate inorganic-inorganic composites with a radio-opaque glass ceramic according to Example 4 and with different amounts of an alkali-silicate glass, the composition of which is given in Table VI. Example 4 was mixed with different amounts of an alkali-silicate-glass (examples 65-69) and example 22 with different amounts of a boro-silicate-glass (examples 70-74). They were mixed in a so-called Turbula-mixer for about 10 to 60 minutes, preferred 30 minutes and sintered at temperatures, given in table VI to form an inorganic-inorganic composite glass ceramic.

The glass transition temperature that was measured according to the procedure that was described for examples 48 to 55, the chemical durability according to the method described for examples 56 to 59 and optical properties. The optical properties of translucency (values between 0 and 1) were determined according to BS 512;1978.

The definitions of the characteristic color values (L, a, b) are given in BS 5612;1978.

By preparing the inorganic-inorganic composites containing another possibility for adjusting the translucence as well as the coefficient of thermal expansion of the resulting products is established as can be seen from the data shown in Table VI.

TABLE VI

Inorganic-inorganic composite materials

| Component | 65 (100% Expl. 4) wt. -% | 66 (75% Expl. 4: 25% alkali-silicate-glass) wt. -% | 67 (50% Expl. 4: 50% alkali-silicate-glass) wt. -% | 68 (25% Expl. 4: 75% alkali-silicate-glass) wt. -% | 69 100% alkali-silicate-glass wt. -% |
|---|---|---|---|---|---|
| $SiO_2$ | 50.8 | 52.2 | 53.6 | 55.0 | 56.4 |
| $P_2O_5$ | 3.7 | 2.8 | 1.9 | 0.9 | — |
| $B_2O_3$ | 0.3 | 2.2 | 4.1 | 6.0 | 7.83 |
| $Al_2O_3$ | 13.2 | 13.1 | 12.9 | 12.8 | 12.7 |
| $Y_2O_3$ | 3.1 | 2.4 | 1.6 | 0.8 | — |
| $ZrO_2$ | 0.8 | 0.9 | 1.0 | 1.0 | 1.1 |
| $TiO_2$ | 0.2 | 0.2 | 0.1 | 0.1 | — |
| $CeO_2$ | 0.7 | 0.7 | 0.6 | 0.6 | 0.5 |
| $Li_2O$ | 0.2 | 0.2 | 0.2 | 0.2 | 0.2 |
| $Na_2O$ | 7.8 | 7.6 | 7.4 | 7.2 | 7.0 |
| $K_2O$ | 10.0 | 10.1 | 10.3 | 10.4 | 10.6 |
| $Rb_2O$ | — | — | — | — | — |
| $Cs_2O$ | — | — | — | — | — |
| CaO | — | 0.3 | 0.5 | 0.8 | 1.1 |
| SrO | 8.5 | 6.4 | 4.3 | 2.1 | — |
| ZnO | — | 0.5 | 1.0 | 1.5 | 2.0 |
| F | 0.7 | 0.7 | 0.7 | 0.7 | 0.7 |
| $TEC_{100-500° C.}/10^{-5} \cdot K^{-1}$ | 14.2 | 12.7 | 11.6 | 10.3 | 8.6 |
| $Tg/°C.$ | 561 | 550 | 535 | 534 | 542 |
| firing temp./° C. | 980 | 980 | 940 | 870 | 850 |
| chem. durability./ $\mu g/cm^2$ | 24.1 | 29.4 | 32.1 | 37.9 | 33.1 |
| optical properties | | | | | |
| L | 90.75 | 90.51 | 89.01 | 85.25 | 75.12 |
| a | −1.47 | −1.57 | −1.77 | −2.07 | −0.33 |
| b | 3.90 | 2.34 | 1.23 | −0.18 | 3.62 |
| CR/% | 88.51 | 88.14 | 74.31 | 57.32 | 8.52 |

| Component Oxide | 70 (100% Expl. 22) wt. -% | 71 (60% Expl. 22: 40% Boro-Silicate-Glass) wt. -% | 72 (40% Expl. 22: 60% Boro-Silicate-Glass) wt. -% | 73 (20% Expl. 22: 80% Boro-Silicate-Glass) wt. -% | 74 (100% Boro-Silicate-Glass) wt. -% |
|---|---|---|---|---|---|
| $SiO_2$ | 48.3 | 59.5 | 65.1 | 70.7 | 76.3 |
| $P_2O_5$ | 3.8 | 2.3 | 1.5 | 0.8 | — |
| $B_2O_3$ | 8.2 | 8.9 | 9.2 | 9.6 | 9.9 |
| $Al_2O_3$ | 11.6 | 9.1 | 7.9 | 6.6 | 5.4 |
| $Y_2O_3$ | 0.5 | 0.3 | 0.2 | 0.1 | — |
| $ZrO_2$ | — | — | — | — | — |
| $TiO_2$ | — | — | — | — | — |
| $CeO_2$ | — | — | — | — | — |
| $Li_2O$ | — | — | — | — | — |
| $Na_2O$ | 6.9 | 6.8 | 6.8 | 6.7 | 6.7 |
| $K_2O$ | 11.2 | 6.8 | 4.6 | 2.4 | 0.2 |
| $Rb_2O$ | — | — | — | — | — |
| $Cs_2O$ | — | — | — | — | — |
| CaO | — | 0.6 | 0.9 | 1.2 | 1.5 |
| SrO | 8.8 | 5.3 | 3.5 | 1.8 | — |
| ZnO | — | — | — | — | — |
| F | 0.7 | 0.4 | 0.3 | 0.1 | — |
| $C.T.E._{100-500° C.}/10^{-6} K^{-1}$ | 9.81 | 7.66 | 6.76 | 6.09 | not measured |
| $Tg/°C.$ | 575 | 577 | 582 | 580 | not measured |
| Firing temperature/° C. | 860 | 880 | 870 | 890 | not measured |
| Chem. durability/ $\mu g * cm^{-2}$ | 132.4 | 79.2 | 56.4 | 37.8 | not measured |

TABLE VI-continued

Inorganic-inorganic composite materials

Optical properties

| | | | | | |
|---|---|---|---|---|---|
| L | not measured | 89.49 | 87.56 | 85.63 | not measured |
| a | not measured | −0.28 | −0.51 | −1.16 | not measured |
| b | not measured | 1.73 | 1.73 | 0.94 | not measured |
| CR/% | not measured | 87.07 | 80.93 | 60.11 | not measured |

The invention claimed is:

1. A method for preparing a dental layering material comprising mixing of a translucent and radio-opaque glass ceramic which comprises

| Component | Wt. % |
|---|---|
| $SiO_2$ | 46.0–58.0 |
| $P_2O_5$ | 2.0–6.0 |
| $Me_2O_3$ | 10.0–22.0 |
| $Me_2O$ | 14.5–30.0 |
| MeO | 4.0–13.0 |
| F | 0.3–3.0, | with $Me_2O_3$ being selected from

| Component | Wt. % |
|---|---|
| $Al_2O_3$ | 8.0–16.0 |
| $Y_2O_3$ | 0.1–9.0 |
| $B_2O_3$ | 0–9.0, |

$Me_2O$ being selected from

| Component | Wt. % |
|---|---|
| $Li_2O$ | 0–3.0 |
| $Na_2O$ | 0–9.0 |
| $K_2O$ | 3.0–14.0 |
| $Rb_2O$ | 0–12.5 |
| $Cs_2O$ | 0–18.0, |

MeO being selected from

| Component | Wt. % |
|---|---|
| MgO | 0–9.0 |
| CaO | 0–2.5 |
| SrO | 0–13.0 | with the proviso that at least one of SrO or MgO $\geq$ 3.1 wt. % if CaO is 0.1 to 2.5 wt.-%,
and which has apatite as a main crystalline phase, with one or more glasses or glass ceramics selected from the group consisting of $SiO_2$—$Al_2O_3$—$K_2O$ based glasses and glass ceramics, $SiO_2$—$B_2O_3$—$Na_2O$ based glasses and glass ceramics, alkali-silicate based glasses and glass ceramics, alkali-zinc-silicate silico-phosphate and/or $SiO_2$—$ZrO_2$ based glasses and glass ceramics.

2. Method according to claim 1, wherein the dental layering material has adjustable optical properties and an adjustable coefficient of thermal expansion.

3. Method according to claim 1, wherein the layering material has a coefficient of thermal expansion in the range between 6 to $20 \times 10^{-6}$ K$^{-1}$, measured in the temperature range of 100 to 500° C.

4. A method of producing a dental restoration comprising the steps of (a) mixing a glass ceramic which comprises

| Component | Wt. % |
|---|---|
| $SiO_2$ | 46.0–58.0 |
| $P_2O_5$ | 2.0–6.0 |
| $Me_2O_3$ | 10.0–22.0 |
| $Me_2O$ | 14.5–30.0 |
| MeO | 4.0–13.0 |
| F | 0.3–3.0, | with $Me_2O_3$ being selected from

| Component | Wt. % |
|---|---|
| $Al_2O_3$ | 8.0–16.0 |
| $Y_2O_3$ | 0.1–9.0 |
| $B_2O_3$ | 0–9.0, |

$Me_2O$ being selected from

| Component | Wt. % |
|---|---|
| $Li_2O$ | 0–3.0 |
| $Na_2O$ | 0–9.0 |
| $K_2O$ | 3.0–14.0 |
| $Rb_2O$ | 0–12.5 |
| $Cs_2O$ | 0–18.0, |

MeO being selected from

| Component | Wt. % |
|---|---|
| MgO | 0–9.0 |
| CaO | 0–2.5 |
| SrO | 0–13.0 | with the proviso that at least one of SrO or MgO $\geq$ 3.1 wt. % if CaO is 0.1 to 2.5 wt.-%,
and which has apatite as a main crystalline phase, (b) applying the mixture of step (a) to a substrate and
(c) firing the coated structure of step (b) to fix the mixture to the substrate.

5. Method according to claim 4, wherein the substrate is a substructure made of metal, metal alloy, glass, glass ceramic or ceramic.

6. Method according to claim 5, wherein the dental restoration is an inlay, an onlay, a bridge, an abutment, a facing, a veneer, a facet, a crown, a partial crown, a framework or a coping.

7. A process for manufacturing a dental restoration comprising
   (a) providing the translucent and radio-opaque glass ceramic which comprises

| Component | Wt. % |
|---|---|
| $SiO_2$ | 46.0–58.0 |
| $P_2O_5$ | 2.0–6.0 |
| $Me_2O_3$ | 10.0–22.0 |
| $Me_2O$ | 14.5–30.0 |
| MeO | 4.0–13.0 |
| F | 0.3–3.0, | with $Me_2O_3$ being selected from

| Component | Wt. % |
|---|---|
| $Al_2O_3$ | 8.0–16.0 |
| $Y_2O_3$ | 0.1–9.0 |
| $B_2O_3$ | 0–9.0, |

$Me_2O$ being selected from

| Component | Wt. % |
|---|---|
| $Li_2O$ | 0–3.0 |
| $Na_2O$ | 0–9.0 |
| $K_2O$ | 3.0–14.0 |
| $Rb_2O$ | 0–12.5 |
| $Cs_2O$ | 0–18.0, |

MeO being selected from

| Component | Wt. % |
|---|---|
| MgO | 0–9.0 |
| CaO | 0–2.5 |
| SrO | 0–13.0 | with the proviso that at least one of SrO or MgO $\geqq$ 3.1 wt. % if CaO is 0.1 to 2.5 wt.-%,
and which has apatite as a main crystalline phase,
   (b) forming the glass-ceramic into a block or blank,
   (c) shaping said block or blank into a dental restoration.

8. Process according to claim 7, wherein the shaping is achieved by a machining process.

9. Process according to claim 8, wherein the machining process is a computer controlled process.

10. Process according to claim 9, wherein the computer-controlled process is a CAD/CAM process.

11. Process according to claim 7, wherein the shaping is achieved by a pressing process.

12. Process according to claim 11, which further comprises
   (d) preparing a mould for a dental framework based on a model of the restoration by the wax-up technology,
   (e) embedding the waxed-up framework containing wax in an embedding material,
   (f) burning out the wax of the embedding material,
   (c') heating up the block or blank and transforming it into a viscous state forming a viscous glass ceramic block or blank and
   (c") pressing the viscous glass ceramic block or into the mould to form the dental framework.

13. A method of preparing a coated dental framework which comprises
   (a) preparing a model of a dental restoration from a framework with a waxed-up coating containing wax,
   (b) embedding the model in an embedding material,
   (c) burning out the wax from the model,
   (d) providing a translucent and radio-opaque glass ceramic which comprises

| Component | Wt. % |
|---|---|
| $SiO_2$ | 46.0–58.0 |
| $P_2O_5$ | 2.0–6.0 |
| $Me_2O_3$ | 10.0–22.0 |
| $Me_2O$ | 14.5–30.0 |
| MeO | 4.0–13.0 |
| F | 0.3–3.0, | with $Me_2O_3$ being selected from

| Component | Wt. % |
|---|---|
| $Al_2O_3$ | 8.0–16.0 |
| $Y_2O_3$ | 0.1–9.0 |
| $B_2O_3$ | 0–9.0, |

$Me_2O$ being selected from

| Component | Wt. % |
|---|---|
| $Li_2O$ | 0–3.0 |
| $Na_2O$ | 0–9.0 |
| $K_2O$ | 3.0–14.0 |
| $Rb_2O$ | 0–12.5 |
| $Cs_2O$ | 0–18.0, |

MeO being selected from

| Component | Wt. % |
|---|---|
| MgO | 0–9.0 |
| CaO | 0–2.5 |
| SrO | 0–13.0 | with the proviso that at least one of SrO or MgO≧3.1 wt. % if CaO is 0.1 to 2.5 wt.-%,
and which has apatite as a main crystalline phase,
(e) forming the glass-ceramic into a block or a blank,
(f) heating up the block or blank and transforming it into a viscous state forming a viscous glass ceramic block or blank and
(g) pressing the viscous glass ceramic block or blank into the mould to coat the framework.

14. A method of producing a dental restoration comprising the steps of
 (a) mixing a layering material obtainable by the method according to claim 1 with a liquid,
 (b) applying the mixture of step (a) to a substrate to form a structure and
 (c) firing the structure of step (b) to fix the mixture to the substrate.

* * * * *